United States Patent
Kim et al.

(10) Patent No.: US 10,245,328 B2
(45) Date of Patent: Apr. 2, 2019

(54) GADOLINIUM COMPLEX COMPRISING DO3A-TRANEXAMIC ACID CONJUGATE

(71) Applicant: KYUNGPOOK NATIONAL UNIVERSITY INDUSTRY-ACADEMIC COOPERATION FOUNDATION, Daegu (KR)

(72) Inventors: Tae-Jeong Kim, Gyeongsan-si (KR); Yong Min Chang, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/110,386

(22) PCT Filed: Jan. 8, 2015

(86) PCT No.: PCT/KR2015/000194
§ 371 (c)(1),
(2) Date: Jul. 7, 2016

(87) PCT Pub. No.: WO2015/105352
PCT Pub. Date: Jul. 16, 2015

(65) Prior Publication Data
US 2016/0331849 A1 Nov. 17, 2016

(30) Foreign Application Priority Data
Jan. 10, 2014 (KR) ......................... 10-2014-0003596

(51) Int. Cl.
*C07D 257/02* (2006.01)
*A61K 49/06* (2006.01)
*A61K 49/08* (2006.01)
*A61K 49/10* (2006.01)
*C07F 5/00* (2006.01)

(52) U.S. Cl.
CPC .......... *A61K 49/108* (2013.01); *A61K 49/106* (2013.01); *C07D 257/02* (2013.01); *C07F 5/00* (2013.01)

(58) Field of Classification Search
CPC .. A61K 49/106; A61K 49/108; C07D 257/02; C07F 5/003
See application file for complete search history.

(56) References Cited

U.S. PATENT DOCUMENTS

2010/0227794 A1   9/2010   Yezdimer et al. ............. 514/9.3

FOREIGN PATENT DOCUMENTS

WO   WO 2008/026937   3/2008
WO   WO 2012/043933   4/2012

OTHER PUBLICATIONS

"Kinematic analysis", http://www.dipanalyst.com/Kinematic%20Analysis/Kinematic%20Analysis.html, accessed Mar. 5, 2018.*
NAM. Bulletin of the Korean Chemical Society, 2014, 35(1), 87-92.*
Cho et al., "One-pot Synthesis of Symmetrical 1,4-Disubstituted Piperazine-2,5-diones", B Kor. Chem. Soc., 25: 415-416, 2004.
Gu et al., "Gd-Complexes of 1,4,7,10-Tetraazacyclododecane-N,N',N'',N'''-1,4,7,10-tetraacetic Acid (DOTA) Conjugates of Tranexamates as a New Class of Blood-Pool Magnetic Resonance Imaging Contrast Agents", J. Med. Chem., 54: 143-152, 2011.
Hee-Kyung Kim et al., "Gadolinium Complex of DO3 A-benzothiazole Aniline (BTA) Conjugate as a Theranostic Agent", Journal oplediocinal Chemistry, 56: 8104-8111, 2013.
International Search Report and Written Opinion issued in PCT/KR2015/000194, dated Apr. 10, 2015.
Ki-Hye Jung et al., "Gd Complexes of DO3A-(Biphenyl-2, 2'—bisamides) Conjugates as MRI Blood-Pool Contrast Agents", Medicinal Chemistry Letters, 3: 1003-1007, 2012.
Laurent et al., "Stability of MRI Paramagnetic Contrast Media: A Proton Relaxometric Protocol for Transmetallation Assessment", Investigative radiology, 36: 115-122, 2001.
Lee et al., "Selective Mono-BOC Protection of Diamines", Synthetic Commun, 37: 737-742, 2007.
Roth et al., "Design, Synthesis, and Evaluation of Indolinones as Triple Angiokinase Inhibitors and the Discovery of a Highly Specific 6-Methoxycarbonyl-Substituted Indolinone (BIBF 1120)", J Med. Chem., 52: 4466-4480, 2009.

* cited by examiner

Primary Examiner — Noble E Jarrell
(74) Attorney, Agent, or Firm — Norton Rose Fulbright US LLP

(57) ABSTRACT

The present disclosure relates to a magnetic resonance imaging (MRI) contrast agent containing a gadolinium complex, and more specically, to a DO3A-tranexamic acid compound having a structure of a chemical formula 1, or an ester compound thereof, and gadolinium complexes thereof. The DO3A-tranexamic acid compound or the ester compound thereof may be used to prepare gadolinium complexes. The gadolinium complexes exhibit thermodynamic and kinetic stabilities, and show the relaxation rate equal to that of the clinical contrast agent which is currently commercially available. Therefore, the gadolinium complexes can be widely used as an MRI contrast agent.

9 Claims, 13 Drawing Sheets

GADOLINIUM COMPLEX COMPRISING DO3A-TRANEXAMIC ACID CONJUGATE

CROSS-REFERENCE TO RELATED APPLICATIONS

This application is a national phase application under 35 U.S.C. § 371 of International Application No. PCT/KR2015/000194 filed 8 Jan. 2015, which claims priority to Korean Patent Application No. 10-2014-0003596 filed 10 Jan. 2014. The entire contents of each of the above-referenced applications are incorporated into the present application by reference.

BACKGROUND

Field of the Present Disclosure

The present disclosure relates to a MRI (magnetic resonance imaging) contrast agent containing a gadolinium complex, and, more particularly, to a DO3A-tranexamic acid compound having a structure of a chemical formula 1, or an ester compound thereof, and gadolinium complexes thereof.

Research Sponsored by Korean Government

The present disclosure is sponsored by Future Creation Science division of Korean Government under a subject No. 2013029618 which is supervised by Korean Research Institute, which belongs to a category "Key Search Support Project", whose title is "HIGH SENSITIVITY CT MOLECULAR IMAGING NANOCOMPOSITE HAVING MULTI-ENERGY BANDWIDTH", and which is conducted by Kyungpook National University (KNU) Industry-academic cooperation foundation between May 1, 2013 and Apr. 30, 2014.

Further, the present disclosure is sponsored by Future Creation Science division of Korean Government under a subject No. 2013069507 which is supervised by Korean Research Institute, which belongs to a category "Fundamental Search Project", whose title is "GADOLINIUM NANO-STRUCTURES FOR NEUTRON CAPTURE THERAPY", and which is conducted by Kyungpook National University Industry-academic cooperation foundation between Dec. 1, 2013 and Oct. 31, 2014.

Discussion of the Related Art

A MRI (magnetic resonance imaging) has been one of the most powerful techniques for non-invasive diagnosis of human anatomy, physiology and pathophysiology based on an excellent spatial resolution and contrast. Currently, a number of MRI techniques use Gd (III) complexes to increase a water proton relaxation rate in the human body to improve the image contrast. Typical advantages resulting from using the Gd (III) ions comes from unique properties such as a high magnetic moment of a long electron spin relaxation time. However, despite extensive and successful clinical applications thereof, most of conventional Gd (III) based contrast agents (GBCAs) are of an extracellular fluid (ECF) contrast agent with a rapid discharge from the kidney. Therefore, there is a need for a new MRI contrast agent having enhanced performance and specific functionality at the same time. A lot of effort has been devoted to develop a new class of MRI contrast agents for use as an organ targeting MRI contrast agent.

A liver-specific MRI contrast agent is divided into following two categories: (i) a hepatobiliary-specific contrast agent and (ii) reticuloendothelial cell- specific (or nanoparticulate) contrast agent. The former contrast agent is absorbed by functional liver cells and released into a bile, and causes the reduction of a longitudinal relaxation time (T1) of the liver and bile tree due to their paramagnetic properties. Currently available contrast agents of this class are based on a Gd-chelate such as Gd-EOB-DTPA (Primovist®) and Gd-BOPTA (Multihance®). When injected, they are initially distributed in the ECF CAs compartment and is subsequently absorbed by the liver cells (hepatocytes). On the other hand, the latter contrast agent targets Kupffer's cells in the endothelial-based system, where phagocytosis of the contrast agent occurs, and an iron ions effect leads to reduction of the liver signal intensity to express a "black" liver instead of a "white" liver that is typically observed in the liver cell-specific contrast agent.

[Chart 1]

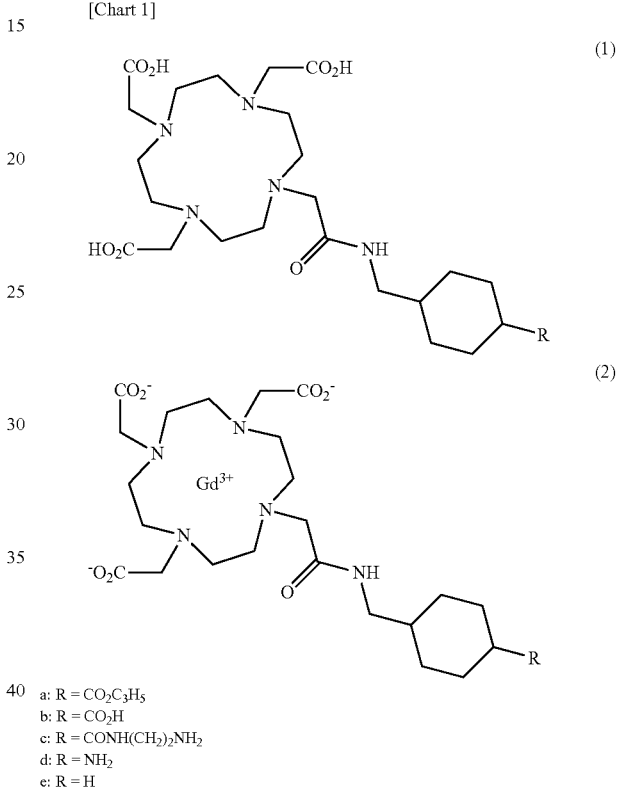

a: R = CO$_2$C$_3$H$_5$
b: R = CO$_2$H
c: R = CONH(CH$_2$)$_2$NH$_2$
d: R = NH$_2$
e: R = H

The present applicants have recently synthesized gadolinium complexes of several DO3A-tranexamate (2a-b, Chart 1) and reported that they exhibit hepatobiliary-specific properties (Gu, S.; Kim, H. K.; Lee, G. H.; Kang, B. S.; Chang, Y.; Kim, T. J. *J. Med. Chem.* 2011, 54, 143.). These observations and recent researches for multi-functional contrast agents have motivated the present applicants to produce several additional DO3A-tranexamates (1c-e) and their corresponding Gd-complexes (2c-e) for use as a new class of a liver-specific contrast agent. The present applicants also have analyzed SAR (structure-activity relationship) for a liver-specificity.

SUMMARY

Thus, the present disclosure is to provide a DO3A-tranexamic acid compound having a structure of a chemical formula 1, or an ester compound thereof.

Further, the present disclosure is to provide a composition for a complex ligand (L) containing the above compound and a gadolinium complex containing the above compound as a ligand.

Furthermore, the present disclosure is to provide a MRI contrast agent containing the gadolinium complex with a high relaxation rate, a thermodynamic and kinematic stability and a pH stability.

In one aspect, the present disclosure provides a DO3A-tranexamic acid compound having a structure of a following chemical formula 1, or an ester compound thereof:

[chemical formula 1]

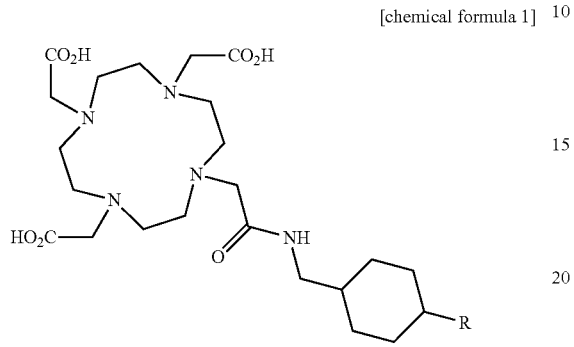

where R is H, $NH_2$ or $CONH(CH_2)_2NH_2$.

In one aspect, the present disclosure provides a method for producing the above-define DO3A-tranexamic acid or the ester compound thereof, wherein $R=CONH(CH_2)_2NH_2$ (compound 1c), wherein the method comprises:
  a) adding and agitating bromoacetyl bromide into trans-4 (aminomethyl)cyclohexaneethylcarboxylate hydrochloride) to form a first mixture;
  b) adding and agitating DO3A-($^t$BuO)$_3$ to the first mixture to produce DO3A ($^t$BuO)$_3$ tranexamic ethyl ester conjugate;
  c) adding 1,2-diaminoethane to the DO3A ($^t$BuO)$_3$ tranexamic ethyl ester conjugate to form a second mixture;
  d) removing a solvent from the second mixture under a low pressure and then dissolving the resultant product in methanol and then performing silica gel chromatography thereto;
  e) adding TFA to the product subjected to the chromatography to deprotect a tert-butyl group; and
  f) drying the thus-resulting product in a vacuum state to obtain the DO3A-tranexamic acid or the ester compound thereof.

In one aspect, the present disclosure provides a method for producing the above-defined DO3A-tranexamic acid or the ester compound thereof, wherein $R=NH_2$ (compound 1d), wherein the method comprises:
  a) adding and agitating di-tert-butyl dicarbonate to trans-1,4-diaminocyclohexane to form a first mixture:
  b) adding and agitating bromoacetyl bromide to the first mixture to form a second mixture;
  c) adding and agitating DO3A-($^t$BuO)$_3$ to the second mixture to produce DO3A ($^t$BuO)$_3$ tranexamic amine conjugate;
  d) removing a solvent from the resultant product under a low pressure and then dissolving the resultant product in methanol and then performing silica gel chromatography thereto;
  e) adding TFA to the product subjected to the chromatography to deprotect a tert-butyl group; and
  f) drying the thus-resulting product in a vacuum state to obtain a DO3A-tranexamicamine compound.

In one aspect, the present disclosure provides a method for producing the above-defined DO3A-tranexamic acid or the ester compound thereof of claim 1, wherein $R=H$ (compound 1e), wherein the method comprises:
  a) adding and agitating bromoacetyl bromide to (aminomethyl)cyclohexane to prepare a first mixture;
  b) adding and agitating DO3A-($^t$BuO)$_3$ to the first mixture to prepare DO3A-($^t$BuO)$_3$ tranexamic conjugate;
  c) removing a solvent from the resultant product under a low pressure and then dissolving the resultant product in methanol and then performing silica gel chromatography thereto;
  d) adding TFA to the product subjected to the chromatography to deprotect a tert-butyl group; and
  e) drying the thus-resulting product in a vacuum state to obtain the DO3A-tranexamic acid or the ester compound thereof.

In one aspect, the present disclosure provides a composition for a complex ligand (L), wherein the composition contains the above-defined DO3A-tranexamic acid or the ester compound thereof.

In one aspect, the present disclosure provides a complex containing the above-defined DO3A-tranexamic acid or the ester compound thereof of claim 1 as a ligand (L), wherein the complex contains a metal atom coordinated with the ligand.

In one embodiment, the metal atom is gadolinium (Gd).

In one aspect, the present disclosure provides a MRI contrast agent containing the above-defined complex as an effective component.

In one embodiment, the contrast agent has ECF (extracelluar fluid) image contrast function. In the embodiment of the present invention, the structure activity relationship (SAR) analysis result of five complexes (2a-e) shows that only the complex 2a exhibits the liver-specificity. Although the complexes 2b and 2c have strong specificity enhancement, they may not exhibit bile-discharge to allow them to be called as the liver-specific contrast agent. The remaining complexes have very similar behaviors to a conventional ECF contrast agent, such as Dotarem®. Further, a new series of the present application may not have any toxicity for use in vivo.

In one embodiment, the contrast agent has high relaxation rate, improved thermodynamic and kinematic stability, and pH stability. This embodiment shows that a new series of the present application has a high kinematic stability over a wide pH range of pH 3 to 11.

Specifically, in the embodiment of the present disclosure, a series of DO3Atranexamate conjugates (1c-e) and Gd complexes (2c-e) thereof for use as liver-specific MRI contrast agents are synthesized. All such complexes exhibit thermodynamic and kinetic stabilities comparable to the clinical contrast agent such as Dotarem®. Further, $R_1$ relaxation rates of the complexes are in a range of 3.68 to 4.84 mM-1s-1 which is comparable to the commercial contrast agent. When the complexes 2a-e are injected into the mice, in vivo MR images of the mice show that only the complex 2a exhibits the liver-specificity. Although the complexes 2b and 2c have strong specificity enhancement, they may not exhibit bile-discharge to allow them to be called as the liver-specific contrast agent. The remaining complexes have very similar behaviors to a conventional ECF contrast agent, such as Dotarem®. Further, a new series of the present application may not have any toxicity for use in vivo.

As described above, the evaluation of the present new series of the liver-specific MRI contrast agents is based on the prior discovery that the complex 2a acts not only as a HAS target but also a kinetic inert biological synthesis chelates of the Gd complex exhibiting a liver-specificity of a certain degree. The present new series of the DO3A-tranexamate conjugates may include the complex 2c-e, and the synthesis thereof is based on a variant of the typical synthesis of the complex 2a. That is, the synthesis of the series 1 may be as follows; initially, a DO3A (tBuO)$_3$ tranexamate conjugate is formed; then, addition of the TFA allow deprotection of a tert-butyl group. The synthesis of the series 2 may be based on the complexing of the gadolinium chloride. These may be referred to FIG. 1 to FIG. 3. The synthesis thereof may be subjected to microanalysis and various spectroscopic tests.

As described above, the present new series of the DO3A tranexamate conjugates (1c-e) and the Gd complexes (2c-e) thereof may be produced to be used as the liver-specific MRI contrast agents. All such complexes exhibit thermodynamic and kinetic stabilities comparable to the clinical contrast agent such as Dotarem®. Further, $R_1$ relaxation rates of the complexes are in a range of 3.68 to 4.84 mM-1s-1 which is comparable to the commercial contrast agent. When the complexes 2a-e are injected into the mice, in vivo MR images of the mice show that only the complex 2a exhibits the liver-specificity. Although the complexes 2b and 2c have strong specificity enhancement, they may not exhibit bile-discharge to allow them to be called as the liver-specific contrast agent. The remaining complexes have very similar behaviors to a conventional ECF contrast agent, such as Dotarem®. Further, the present new series of the present application may not have any toxicity for use in vivo.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
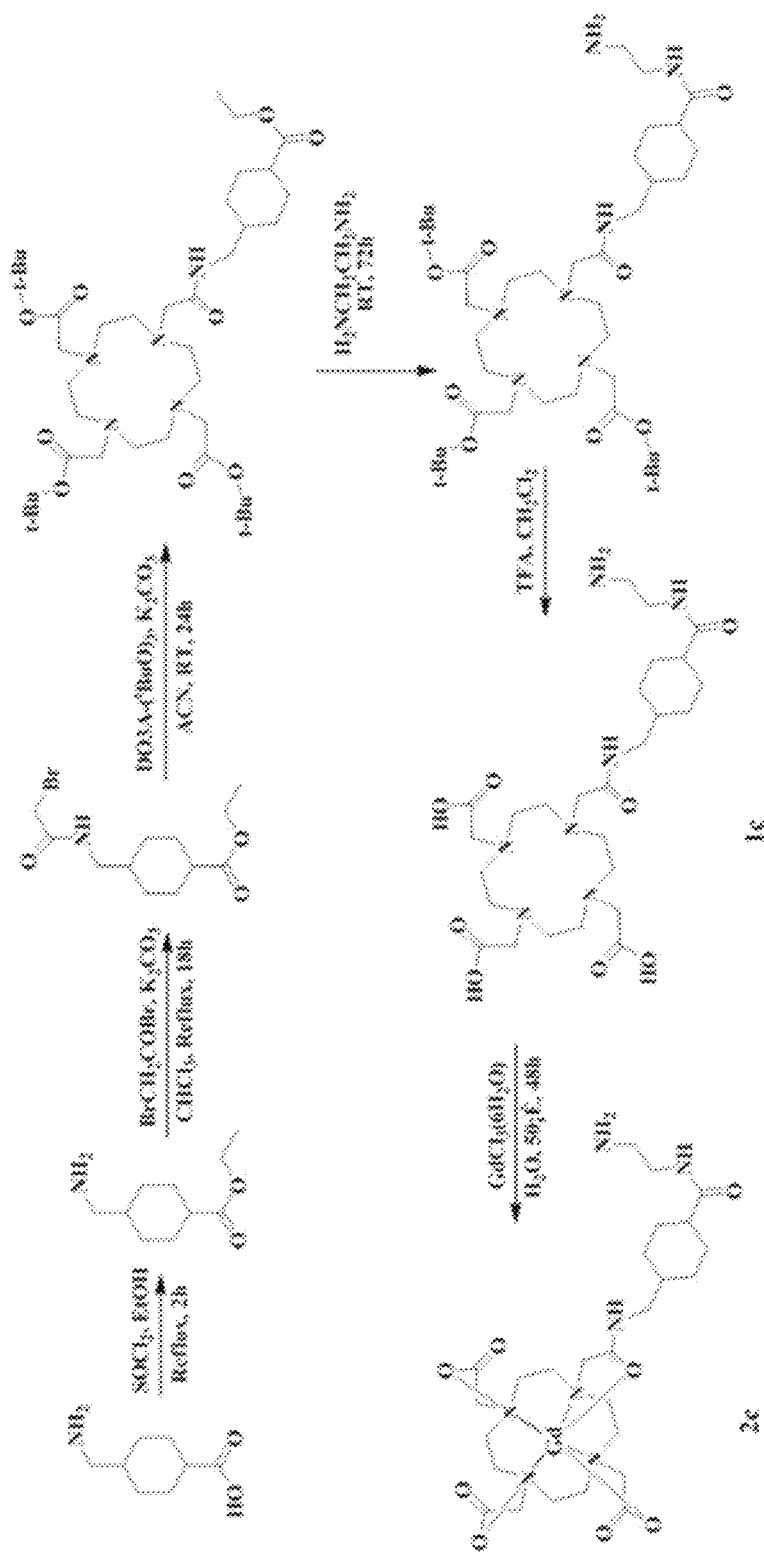
FIG. 1 shows a synthesis diagram of a DO3A-tranexamic acid (1c) and a gadolinium complex (2c) thereof in accordance with the present disclosure.
Figure 2:
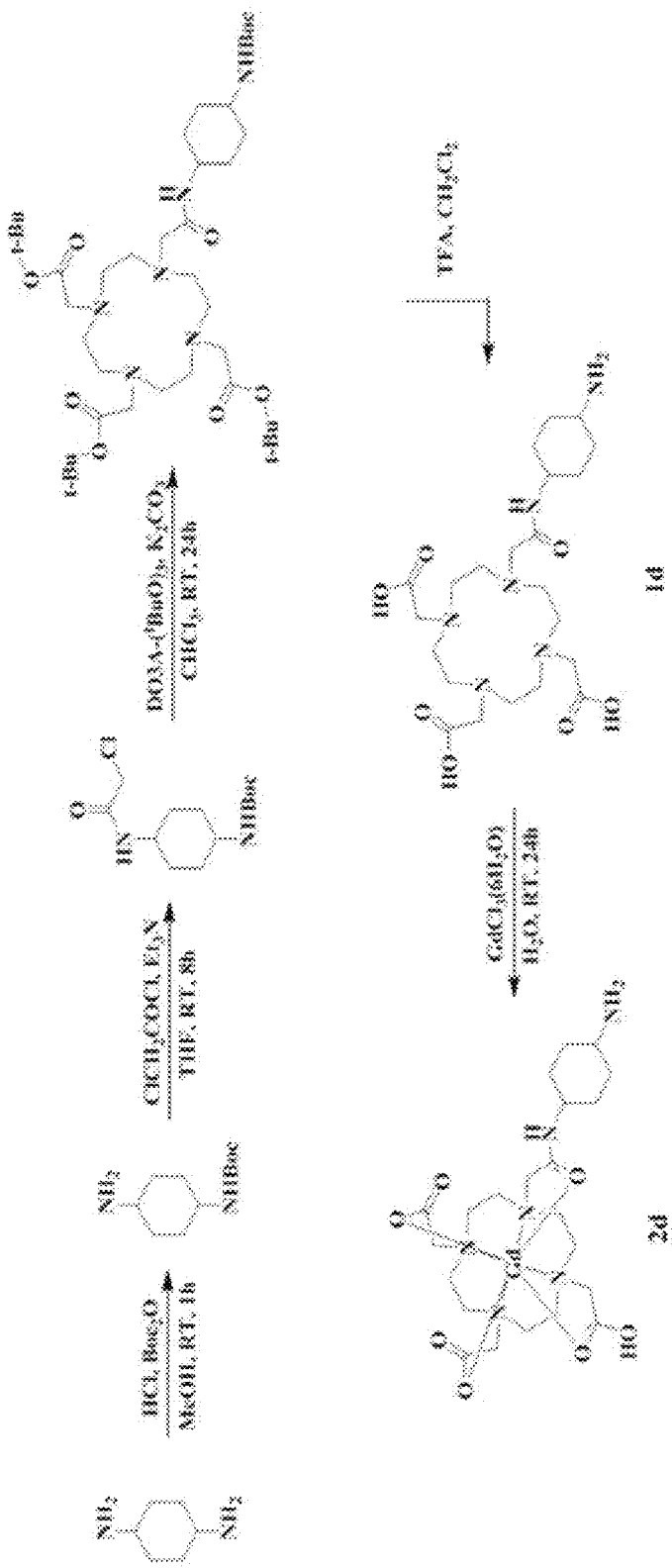
FIG. 2 shows a synthesis diagram of a DO3A-tranexamic acid (1d) and a gadolinium complex (2d) thereof in accordance with the present disclosure.
Figure 3:
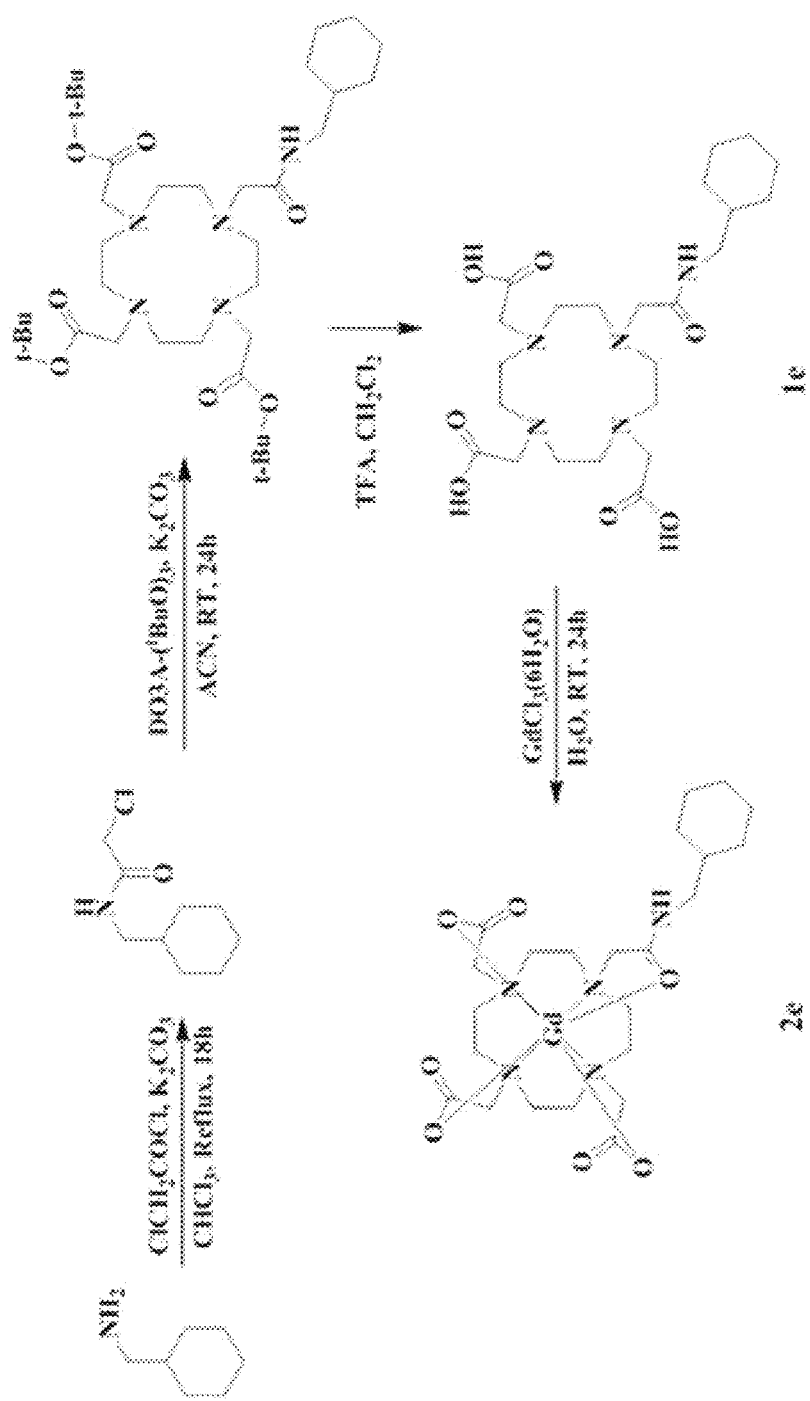
FIG. 3 shows a synthesis diagram of a DO3A-tranexamic acid (1e) and a gadolinium complex (2e) thereof in accordance with the present disclosure.

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

In present embodiments, all reactions were performed under a dinitrogen atmosphere using a standard Schlenk techniques. Solvents were purified and dried by standard procedures. 1,4,7,10-tetraazacyclododecane (DOTA) was purchased from Strem (US), and trans-4-(aminomethyl)-cyclohexane carboxylic acid (tranexamic acid) and trans-1, 4-diamino cyclohexane were purchased from Aldrich, and aminomethyl cyclohexane was purchased from TCI. All other commercial reagents were purchased and received and used from Aldrich unless otherwise specified. deionized water (DI water) was used for all experiments. A 1H experiment was carried out on a Bruker Advance 400 or 500 spectrometer in KBSI. Chemical shifts were given as a δ value as a comparison value to tetramethylsilane (TMS) as an internal standard. A coupling constant is represented by Hz, and FAB mass spectra were obtained using a JMS-700 model (Jeol, Japan) mass spectrophotometer. MALDI-TOF mass spectra were obtained using a Voyager DE-STR (Applied Biosystems, U.S.). Elemental analysis was performed at the Center for Scientific Instruments of KNU (Kyungpook National University).

[Chart 1]

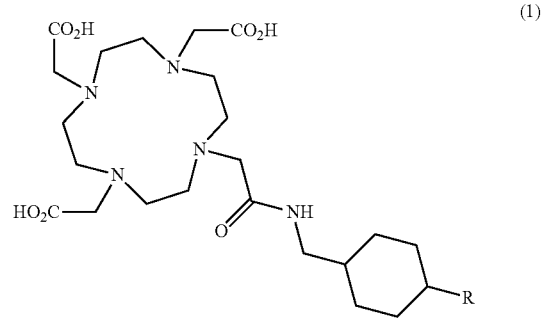

(1)

-continued

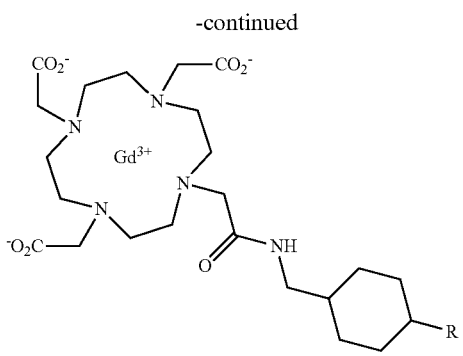

(2)

a: R = CO₂C₃H₅
b: R = CO₂H
c: R = CONH(CH₂)₂NH₂
d: R = NH₂
e: R = H

Embodiment 1: Ligand Synthesis

1) Synthesis of Compounds 1a and 1b

The compounds 1a and 1b are prepared using a previous document (Gu, S.; Kim, H. K.; Lee, G. H.; Kang, B. S.; Chang, Y.; Kim, T. J. *J. Med. Chem.* 2011, 54, 143).

2) Synthesis of Compound 1c

First, using a previous document method (Gu, S.; Kim, H. K.; Lee, G. H.; Kang, B. S.; Chang, Y.; Kim, T. J. *J. Med. Chem.* 2011, 54, 143), DO3A ($^t$BuO)$_3$ tranexamic ethyl ester conjugate (6.8 mmol) (cf, R=CO₂Et, Chart 1) is prepared. The DO3A ($^t$BuO)$_3$ tranexamic ethyl ester conjugate is added to a neat 1,2-diaminoethane (2.3 mL, 33.8 mmol) to form a mixture. The mixture is agitated at a room temperature (RT) for 72 hours, to which chloroform is added, and, the resultant product is extracted using water (30 mL×3 times). The organic extract is dried on MgSO₄, and filtered and evaporated to produce a crude product which in turn, is subjected to a silica chromatography (gradient elution CH₂Cl₂ to 10% MeOH—CH₂Cl₂, R$_f$=0.6 (MeOH/CH₂Cl₂=2:8)) to obtain a yellow solid. This solid is dissolved in (10 mL) and, then, trifluoroacetic acid (TFA) was added to the solution to deprotect a tert-butyl group. The mixture is agitated for one night at a room temperature, and, then, the solvent is removed from the mixture solution in a vacuum state to leave only an oily residue. The, water is absorbed into this residue. Then, acetone is added thereto to allow a white solid to precipitate as a product. Then, the product is subjected to multiple acetone cleanings, and, then, dried at a vacuum state: yield: 0.36 g (92%).

1H NMR (D₂O): δ=3.82 (s, 4H, —NCH₂CO₂—), 3.62 (2H, —NCH₂CO₂—), 3.67 (s, 2H, —CH₂CON), 3.44 (m, 10H, overlapped —NCH₂CH₂N— in the ring (8H) & CONHCH₂— (2H)), 3.08 (d, 2H, —CONHCH-2C—), 2.24/1.52 (m, 2H, —CONH), 1.85/1.41 (m, 8H, —CH₂—, cyclohexyl), 1.03 (m, 2H, —CH₂—, cyclohexyl). Anal. Calcd for C₂₆H₄₇N₇O₈2H₂O: C, 50.23; H, 8.27; N, 15.77. Found: C, 50.66; H, 8.24; N, 16.01. MALDI-TOF MS (m/z): Calcd for C₂₆H₄₇N₇O₈: 585.35, Found: 586.74 ([MH]+), 608.70 ([MNa]+).

3) Synthesis of Compound 1d

First, DO3A- ($^t$BuO)₃ (1.6 g, 3.1 mmol) is added to trans-[4-(2-chloroacetylamino)cyclohexyl]carbamic tert-butyl ester (1.0 g, 3.4 mmol) solution among chloroform (100 mL) prepared from trans-1,4-cyclohexane using a previous document method (Lee, D. W.; Ha, H. J. *Synthetic Commun* 2007, 37, 737 Roth, G. J.; Heckel, A.; Colbatzky, F.; Handschuh, S.; Kley, J.; Lehmann-Lintz, T.; Lotz, R.; Tontsch-Grunt, U.; Walter, R.; Hilberg, F. *J. Med. Chem.* 2009, 52, 4466). The mixture is agitated at a room temperature for 24 h, and all solids are removed and a filtered liquid is evaporated in a vacuum to leave a yellow oily residue. This residue is subjected to silica column chromatography (gradient elution: CH₂Cl₂ to 10% MeOH—CH₂Cl₂, R$_f$=0.4 (MeOH/CH₂Cl₂=1:9)) to get an off-white solid. This solid is re-dissolved in dichloromethane and then a considerable amount of TFA is added thereto. After the product is agitated for one night, and a methanol is added thereto to precipitate a white solid. Then, the final product is more purified using a typical purification method: yield: 0.62 g (87%).

1H NMR (D₂O): δ=3.72 (m, 10H, overlapped —NCH₂CO₂— (8H), —CONHCH— & H₂NCH— (2H)), 3.40/3.21 (m, 16H, —NCH₂CH₂N—), 2.06/1.55/1.38 (m, 8H, —CH₂—, cyclohexyl). Anal. Calcd for C₂₂H₄₀N₆O₇2CF₃COON2H₂O: C, 39.00; H, 6.29; N, 10.50. Found C, 39.13; H, 6.05; N, 9.35. MALDI-TOF MS (m/z): Calcd for C₂₂H₄₀N₆O₇: 500.30, Found: 501.33 [MH]+, 523.33[MNa]+.

4) Synthesis of Compound 1e

First, DO3A-($^t$BuO)₃ (3.0 g, 5.8 mmol) is added to 2-cloro-N-cyclohexilmethylacetamid (1.2 g, 6.4 mmol) solution among acetonitrile (30 mL) prepared using a previous document method (Cho, S. D.; Song, S. Y.; Kim, K. H.; Zhao, B. X.; Ahn, C.; Joo, W. H.; Yoon, Y. J.; Falck, J. R.; Shin, D. S. *B Kor. Chem. S° C.* 2004, 25, 415). The mixture is agitated at a room temperature for 24 h, and all impurity solids are removed and a filtered liquid is evaporated in a vacuum to leave a yellow oily residue. This residue is subjected to a silica column chromatography (gradient elution: CH₂Cl₂ to 10% MeOH—CH₂Cl₂, R$_f$=0.4 (MeOH/CH₂Cl₂=1:9)). Then, the evaporation is applied thereto under a pressure reduction to obtain an off-white solid. As in the synthesis of the compound 1d, the TFA is added thereto to deprotect a tert-butyl group to obtain an off-white solid as a final product. yield: 2.4 g (82%).

1H NMR (D₂O): δ=3.74/3.57 (m, 8H, —NCH₂CO₂—), 3.30 (m, 10H, overlapped NCH₂CH₂N— (8H) & CONHCH₂— (2H)), 3.10 (m, 8H, —NCH₂CH₂N—), 1.98/1.44/1.27 (m, 4H, —CH₂—, cyclohexyl), 1.88 (m, 1H, —NHCH₂CH—). Anal. Calcd for C₂₂H₃₉N₅O₇3CF₃COOH3H₂O: C, 38.14; H, 5.49; N, 7.94. Found: C, 37.83; H, 5.76; N, 8.44. MALDI-TOF MS (m/z): Calcd for C₂₂H₃₉N₅O₇,: 485.28, Found: 486.42 ([MH]+), 508.44 ([MNa]+).

Embodiment 2: Synthesis of Gd Complex

1) Synthesis of Complexes 2a and 2b

The complexes 2a and 2b are prepared using a previous document (Gu, S.; Kim, H. K.; Lee, G. H.; Kang, B. S.; Chang, Y.; Kim, T. J. *J. Med. Chem.* 2011, 54, 143).

2) Synthesis of Complex 2c

First, gadolinium chloride (0.64 g, 1.7 mmol) is added to water (50 mL) 1c (1.0 g, 1.7 mmol) solution and the mixture is agitated at 50° C. for 48 h. pH is checked periodically and thus the pH is adjusted to 7.0 to 7.5 using 1 N NaOH. The reaction mixture is dried at a vacuum state to leave an oily residue. Water is absorbed in the residue. Acetone is added thereto to precipitate a white solid. This solid is filtered and cleaned using acetone and the product is dried at a vacuum state. A hygroscopic ivory solid is obtained as a final product: yield: 0.75 g (86%).

Anal. Calcd for C₂₆H₄₄GdN₇O₈2CF₃COOH8H₂O: C, 32.40; H, 5.62; N, 8.82. Found: C, 31.99; H, 5.22; N, 9.00. HR-FABMS (m/z): Calcd for C₂₆H₄₅GdN₇O₈, 741.26 ([MH H₂O]+). Found: 741.2567; Calcd for C₂₆H₄₄GdN₇O₈Na, 763.24 ([MNa H2O]+). Found: 763.2397.

3) Synthesis of Complex 2d

This synthesis process is the same as in the synthesis process in the complex 2c except that the compound 1c is replaced with the compound 1d. A hygroscopic off-white solid is obtained as a final product: yield: 1.15 g (88%).

Anal. Calcd for $C_{22}H_{37}GdN_6O_7 2CF_3COOH 5H_2O$: C, 32.10; H, 5.08; N, 8.64. Found: C, 31.55; H, 5.09; N, 9.06. HR-FABMS (m/z): Calcd for $C_{22}H_{38}GdN_6O_7$, 656.21 ([MH H2O]+). Found: 656.2045; Calcd for $C_{26}H_{44}GdN_7O_8Na$, 678.19 ([MNa H2O]+). Found: 678.1867.

3) Synthesis of Complex 2e

This synthesis process is the same as in the synthesis process in the complex 2c except that the compound 1c is replaced with the compound 1e. A hygroscopic off-white solid is obtained as a final product: yield: 0.75 g (86%).

Anal. Calcd for $C_{23}H_{38}GdN_5O_7 4H_2O$: C, 38.06; H, 6.39; N, 9.65. Found: C, 38.59; H, 6.09; N, 9.69. HR-FAB MS (m/z): Calcd for $C_{23}H_{39}GdN_5O_7$, 655.21 ([MH H2O]+). Found: 655.2093.

Embodiment 3: Relaxation Rate Measurement

T1 measurement is carried out using an inversion recovery method at 1.5 T (64 MHz) in a variable inverse time (TI). MR images are obtained for 35 different TI values in a range of 50 to 1750 ms. A T1 relaxation time is obtained from a nonlinear least-squares fit of a signal strength measured at each TI value. For a T2 CPMG (Carr-Purcell-Meiboon-Gill) pulse sequence measurement, the measurement is adapted to a multi spin-echo measurement. 34 images are obtained at 34 different echo time (TE) values in a range of 10 to 1900 ms. The T2 relaxation time is obtained from a nonlinear least-squares fit of mean pixel values for multi spin-echo measurement at each echo time. Next, a relaxation rate ($R_1$ and $R_2$) is calculated as an inverse of a relaxation time per mM. The determined relaxation time (T1 and T2) and relaxation rate ($R_1$ and $R_2$) are subjected to an image processing to get a relaxation time map and relaxation rate respectively.

The complexes 2a-e exhibit R1 relaxation rates with PBS which are comparable to those of clinically available MRI contrast agents such as Gd-DOTA (Dotarem®) and Gd-BT-DO3A (Gadovist®) or which are superior to those of the Gd-DOTA (Dotarem®) and Gd-BT-DO3A (Gadovist®) (Tablet). For comparison between the complexes 2a-e, there is no noticeable difference in $R_1$'s. The measurement is carried out for two different media, that is, PBS (pH=7.4) and PBS solution of HAS in order to indicate which bloodpool effect is expressed by the complexes 2a-e. Compared to $R_1$'s in the PBS, $R_1$ in the HAS exhibits meaningful increase, which indicates that there is a little interaction between the present new series and the HAS.

TABLE 1 in PBS and 0.67 mM HAS, relaxation rate data of complexes 2a-e, Gd-DOTA and Gd-BT-DO3A (64 MHz, 293K)

| | $R_1$ (mM$^{-1}$s$^{-1}$) | $R_2$ (mM$^{-1}$s$^{-1}$) | $R_1$ (mM$^{-1}$s$^{-1}$) in 0.67 mM HSA | $R_2$ (mM$^{-1}$s$^{-1}$) in 0.67 mM HSA |
|---|---|---|---|---|
| 2a | 4.84 ± 0.18 | 4.91 ± 0.25 | 5.11 ± 0.10 | 6.04 ± 0.13 |
| 2b | 3.87 ± 0.11 | 3.98 ± 0.26 | 3.98 ± 0.14 | 5.43 ± 0.28 |
| 2c | 3.68 ± 0.13 | 3.62 ± 0.26 | 3.74 ± 0.07 | 4.10 ± 0.07 |
| 2d | 3.94 ± 0.13 | 3.68 ± 0.29 | 3.91 ± 0.09 | 4.07 ± 0.09 |
| 2e | 4.49 ± 0.18 | 4.52 ± 0.28 | 5.21 ± 0.23 | 6.22 ± 0.28 |
| Dotarem* | 3.59 ± 0.17 | 3.87 ± 0.20 | 4.05 ± 0.13 | 4.30 ± 0.25 |
| Gadovist* | 4.38 ± 0.15 | 4.27 ± 0.30 | 4.81 ± 0.17 | 5.54 ± 0.24 |

Embodiment 4: Transmetalation Kinetics

This experiment is prepared using a previous document method (Laurent, S. Elst, L. V.; Copoix, F.; Muller, R. N. *Investigative radiology* 2001, 36, 115). This is based on measurements of evolution of a water proton longitudinal relaxation rate ($R_1P$) of a buffer solution (phosphate buffer, pH 7.4) containing 2.5 mmol/L gadolinium complex and 2.5 mmol/L $ZnCl_2$. Next, 10 μL $ZnCl_2$ 250 mmol/L solution is added to a 1 nk paramagnetic complex buffer solution. The mixture is strongly agitated, and then, 300 μL thereof is taken for a relaxation measurement (relaxometric measurement). Comparison the present series with Gd-DOTA, Gd-BOPTA, Gd-DTPA-BMA, and Gd-EOB-DTPA shows the same results from the presence of $ZnCl_2$. A $R_1P$ relaxation rate is acquired by excluding a diamagnetic contribution of a water proton relaxation from the measured relaxation rate $R_1=(1/T1)$. The measurement is performed at a room temperature on a 3T whole body system (Magnetom Tim Trio, Simens, Korea Institute of Radiological & Medical Science).

Figure 4:
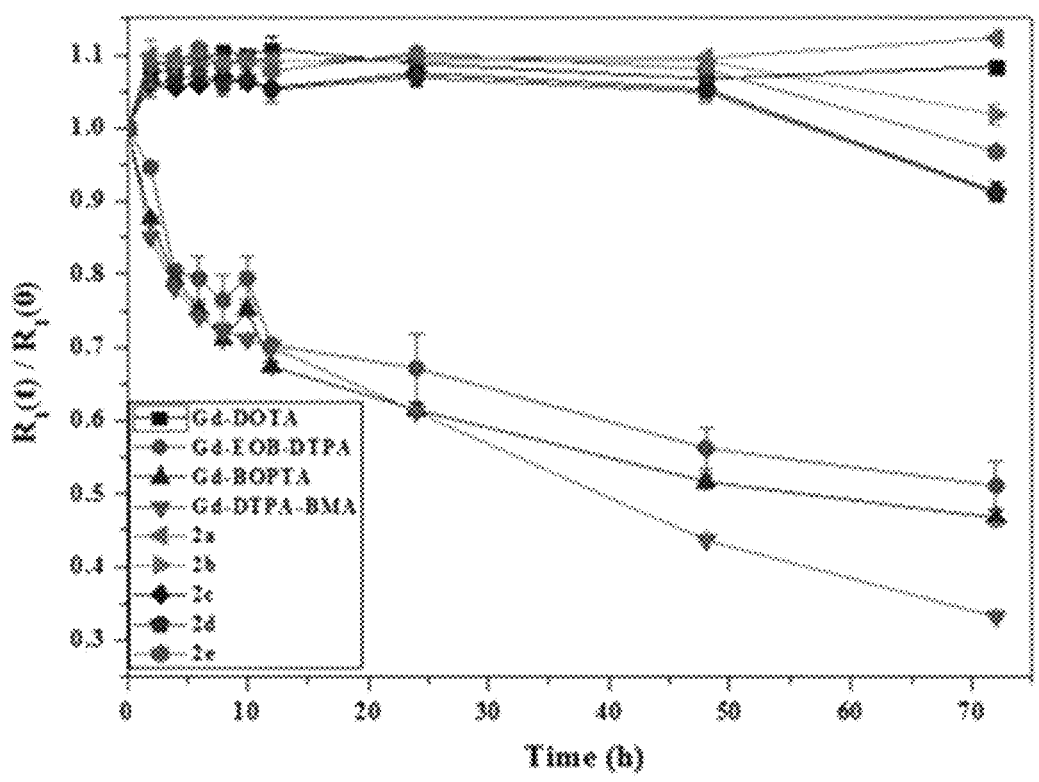
FIG. 4 shows a graph illustrating an evolution of $R_1P$ (t)/$R_1P$ (0) for various MRI contrast agents as a function of a time.

FIG. 4 shows a graph illustrating an evolution of $R_1P$ (t)/$R_1P$ (0) for various MRI contrast agents as a function of a time.

An evaluation of a normal paramagnetic longitudinal relaxation rate $R_1P$ (t)/$R_1P$ (0) is observed between the present series 2a-e and comparison examples Dotarem®, Primovist®, Multihance®, and Omniscan® (FIG. 4). The used complex in the test is divided into two following groups based on an evolution pattern: (i) a group employing a macrocyclic chelate (ii) a group employing an acyclic chelate. The present series complexes employ the macrocyclic chelate and may be highly likely to have very high kinetic inertness and, thus, keep a 90% or larger portion of the paramagnetic relaxation rate at an initial measurement for 72 h. However, for the group employing the acyclic chelate, the relaxation rate is remarkably reduced. For example, Primovist®, and Multihance® has a rapid slope to keep only a 50% portion of the paramagnetic relaxation rate at an initial measurement for 72 h.

Embodiment 5: Isothermal Titration Calorimeter (ITC)

In order to quantify binding isotherms of paramagnetic metal ions $Gd^{3+}$ with a ligand solution, an ITC test is executed at a VP-ITC isothermal titration microcalorimeter (Microcal, USA). Data collection, analysis and plotting are executed with help of software package Origin, version 8.0 from Microcal. A sample cell has a 1.43 mL volume. The cell is filled with a water-soluble buffer solution of the above compound 1a-e ligand (0.2 mM). A water-soluble buffer solution of $Gd^{3+}$ (1.0 mM) is input into a 300 μL continuous agitated (300 rpm) syringe and 10 μL aliquots thereof is injected into the cell. At a 3-mins interval, the cell is delivered over 20 s. Data points are collected on a 2 s basis. The measurement is executed at 25° C. All titrations are executed three times to secure data consistency and solution stability. These titration isotherms are integrated to find out an enthalpy change at each injection. In order to fit well with two mathematically different sets of site models, the titration isotherms are analyzed. Via a calorie measurement, parameters including a binding constant (Ka), a change in enthalpy (ΔH), a stoichiometry of binding (N) are calculated. Next, a free energy (ΔG) and an entropy change (ΔS) are calculated using a following complexation equation:

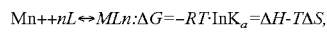

$$Mn + nL \leftrightarrow MLn : \Delta G = -RT \ln K_a = \Delta H - T\Delta S,$$

where, R indicates a universal gas constant; T is Kelvin temperature.

It may be noted that due to the fact that the present series have fourth order high binding constants ($K_a$) from measurements using ITC (Isothermal titration calorimeter), the present series have high thermodynamic stability (See Tablet and FIG. 7). For comparisons between the present series, the compound 1b expresses the highest preference to $Gd^{3+}$ ions for an unknown reason.

FIG. 7A to FIG. 7E show ITC determination of binding thermodynamics of $Gd^{3+}$ to the ligand. A binding isotherm corresponds to a plot of an integral heat as a function of a molar ratio of $Gd^{3+}$/1a-e. A solid line corresponds to the best fit curve of data into one set of mathematically determined site models and indicates one molecule ($Gd^{3+}$) being coupled to a respective ligand. A dissociation constant (Kd), an association constant (Ka), the number of $Gd^{3+}$ coupled to a single ligand (N), and a united enthalpy change (ΔH) are obtained by analysis of data. The dissociation and association constants are critical factors for determining a relative stability compared to a ligand (1a-e).

TABLE 2 titration data of $Gd^{3+}$ (0.2 mM) into water and water-soluble compounds 1a-e (1.0 mM) at 25° C. and pH = 4.5

| | 1a | 1b | 1c | 1d | 1e |
|---|---|---|---|---|---|
| $K_a$ ($10^4 M^{-1}$) | 5.19 | 25.10 | 5.97 | 3.41 | 8.71 |
| $K_d$ ($10^{-6} M$) | 19.27 | 3.98 | 16.75 | 29.33 | 11.48 |
| N | 0.89 | 0.37 | 0.28 | 0.19 | 0.49 |
| ΔH (kcal · mol$^{-1}$) | 4.19 | 7.13 | 5.94 | 4.33 | 3.84 |
| ΔS (cal · mol$^{-1}$ · K$^{-1}$) | 35.60 | 48.60 | 41.80 | 35.30 | 35.50 |
| ΔG (kcal · mol$^{-1}$) | −6.42 | −7.35 | −6.52 | −6.19 | −6.74 |

Embodiment 6: In Vivo MR Experiment

The in vivo experiment is executed with compliance to a regulation of Animal Research Committee of KNU. 29-31 g weight 6-weeks male ICR mice are used. The mice (n=3) are anesthetized with 1.5% isoflurane in oxygen. The measurement is carried out before and after the injection of the complexes 2a-e through the tail vein. The amount of the contrast agent per each injection is as follows: 0.1 mmol Gd/kg for a MR image. After the mice wake from the anesthesia after each measurement, the mice were placed in a cage capable of free access to feed and food. For this measurement, the animals are held at about 37° C. using a warm water blanket. MR images are taken using a 1.5 T MR unit (GE Healthcare, Milwaukee, Wis.) with a manual RF coil for a small animal. The coil may be of a receiver type having a 50 mm inner diameter. Imaging parameters of the spin echo (SE) are as follows: repetition time (TR)=300 msec; echo time (TE)=13 msec; 8 mm field of view (FOV); 192×128 matrix size; 1.2 mm slice thickness; acquisition number (NEX)=8. MR images are collected for 24 h after the injection. Anatomical positions having an improved contrast are set for a liver, a bile duct, and a kidney on (post contrast) MR images. For quantitative measurements, a signal intensity in a region of interest (ROI) is measured using Advantage Window software (GE medical, U.S.). The CNR is calculated using a following equation (1):

$$CNR = SNR_{post} - SNR_{pre} \quad (1)$$

where SNR is a sound-to-noise ratio.

Figure 5:
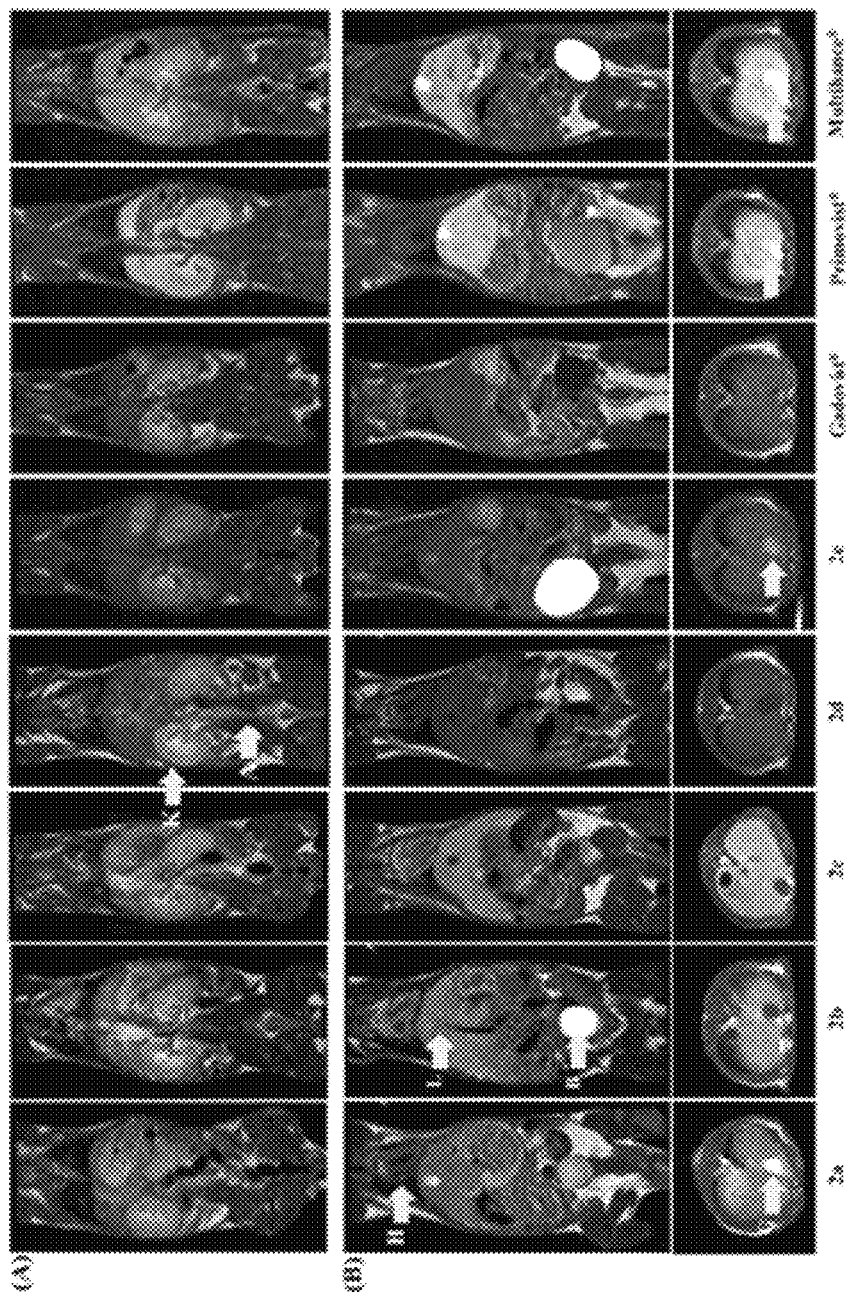
FIG. 5A shows coronal and axial T1-weighted images of ICR mice in five minutes after the present contrast agent is injected thereto, where K indicates a kidney; A indicates abdominal aorta.
FIG. 5B shows coronal and axial T1-weighted images of ICR mice in one hour after the present contrast agent is injected thereto, where A indicates heart; L=liver; B=urinary bladder; G=gallbladder.

FIG. 5A shows coronal and axial T1-weighted images of ICR mice in five minutes after the present contrast agent is injected thereto, where K indicates a kidney; A indicates abdominal aorta. FIG. 5B shows coronal and axial T1-weighted images of ICR mice in one hour after the present contrast agent is injected thereto, where A indicates heart; L=liver; B=urinary bladder; G=gallbladder.

Figure 8:
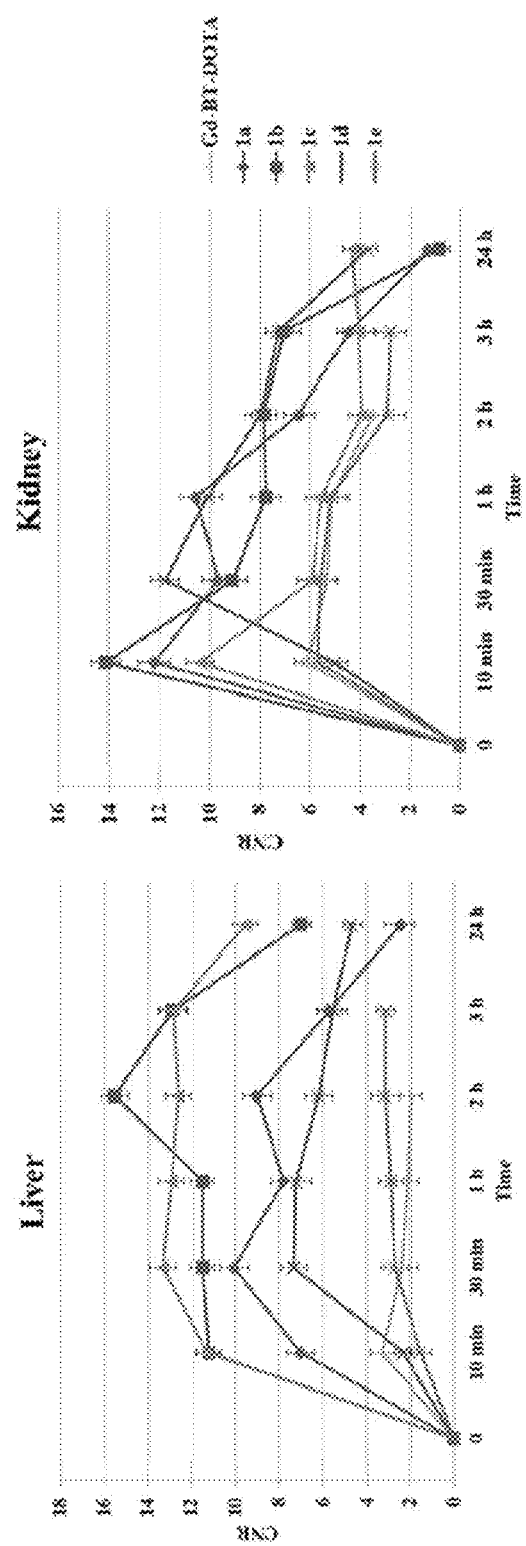
FIG. 8 shows CNR profiles for a liver and kidney, obtained using various contrast agents.

FIG. 8 shows CNR profiles for a liver and kidney, obtained using various contrast agents.

For the complexes 2a to 2e, a strong signal enhancement is observed at the heart and abdominal aorta within 5 mins (FIG. 5A). Among the complexes 2a to 2e, the complexes 2a to 2c exhibit signal enhancements for initial 1 hour for a liver. Thus, the complexes 2a to 2c may be comparable to the typical liver-specific contrast agents such as Primovist® and Multihance®. However, compared to Primovist® and Multihance®, only the complex 2a may be discharged via the bile. Thus, only the complex 2a may be considered as a true liver-specific contrast agent (FIG. 5B). Although the complex 2a also may be discharged via the bile, the signal strength is insufficient to be qualified as the liver-specific contrast agent. The complex 2a has the signal strength as weak as that of Gadovist® as a typical ECF contrast agent (FIG. 5A). Although the complex 2d expresses a strong signal enhancement at both the kidney and abdominal aorta initially, the complex 2d is completely discharged within one hour like Gadovist®. Thus, the complex 2d may be considered as a ECF contrast agent. Although the complexes 2b and 2c express a strong signal enhancement at the liver (FIG. 5A and FIG. 8), a discharge thereof via the bile is not observed. In order to describe this abnormal behavior of the complexes 2b and 2c, two following assumptions are set: the complexes 2b and 2c are input through organic anion transporting polypeptide (OATP) into the liver cells and then, multi-drug resistance protein 2 (MRP2) present as transporting molecules in a membrane between the cells can's transport the complexes 2b and 2c; or the multi-drug resistance protein 2 (MRP2) together with the complexes 2b and 2c may return through the MRP3 or bidirectional OATP to liver sinusoids.

It is noted that for the Primovist® and Multihance® as typical liver-specific contrast agent, a passive diffusion takes place through OATP1 present in the base membrane in normal liver cells. Then, the agent may be discharged to the bile via MRP2 action. For the Primovist® and Multihance®, the presence of a lipophilic ethoxy benzyl is believed to play an important role in the above process. In this respect, it is possible that, for the complex 2a, the presence of lipophilic cyclohexil may play a similar role to the above. This issue requires an additional research.

Embodiment 7: Cell Viability Measurement

Normal conjunctival fibroblast cells are used. The cells are kept in DMEM (Gibco®) supplemented with heat-inactivated FCS (10%), penicillin (100 IU/mL), streptomycin (100 mg/mL), and gentamicin (200 mg/mL) (all of which are purchased from Gibco®). The medium is replaced every 2 days, and the cells are dispensed in a 96-well plate (1×10⁴ cells/well/200 μL). The contrast agent with various Gd (III) concentrations (50 to 500 μM) is added into a serum-free culturing medium and is incubated for 24 h. Next, CCK-8 (10 μL) is added to each well and then, the cell viability is evaluated. The solution is removed at 37° C. after 4 h. Using a microplate reader (Molecular Device, USA Bio-rad Reader 550), an O.D. (Optical Density) value is read at 450 nm and the cell viability/toxicity is determined.

Figure 6:
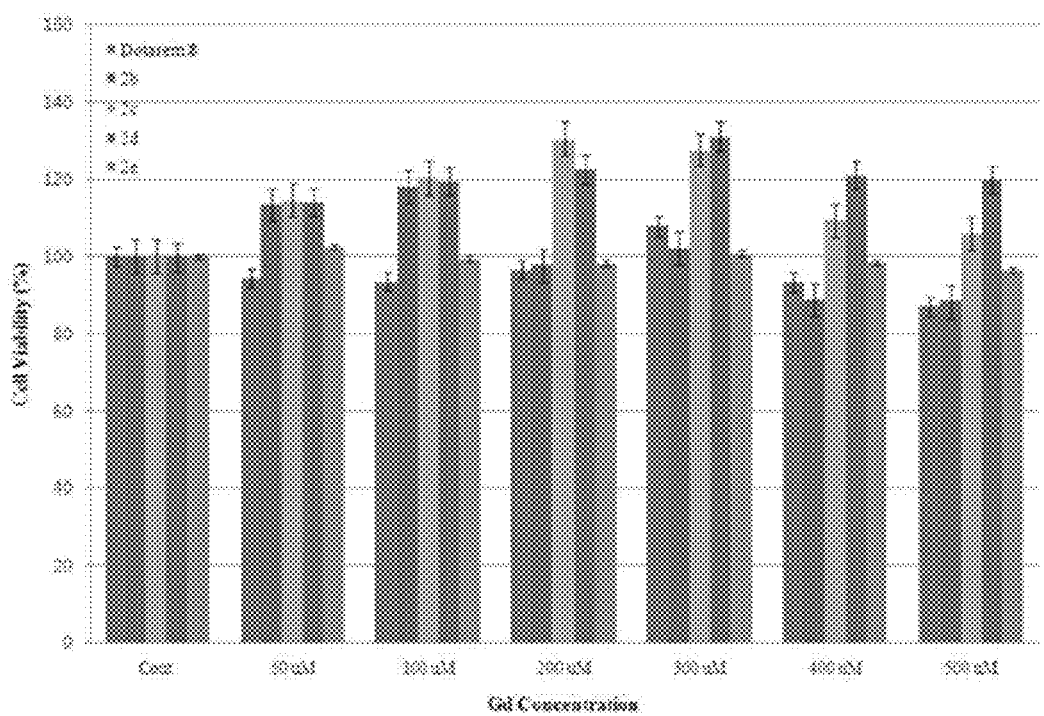
FIG. 6 shows a relative cell toxicity (%) of a normal conjunctival fibroblast obtained using Gd-DOTA and 2b-2. A standard deviation (±SD) is obtained using a triple analysis (n=3).
Figure 7A:
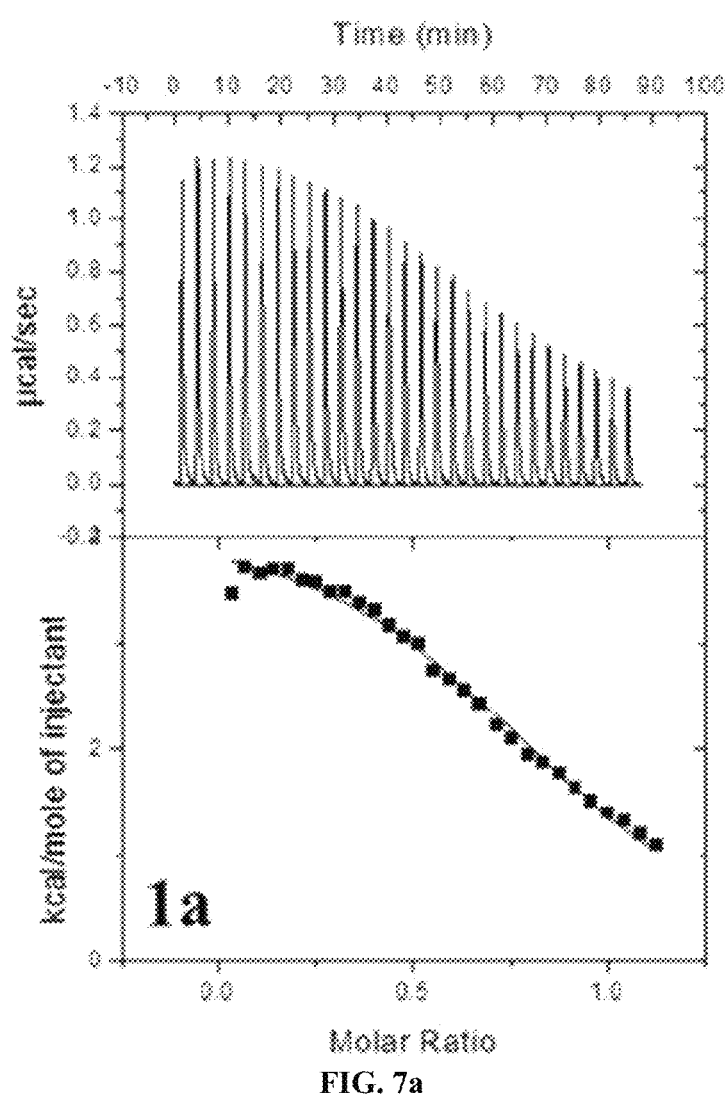
FIG. 7A to FIG. 7E show ITC determination of binding thermodynamics of $Gd^{3+}$ to the ligand. A binding isotherm corresponds to a plot of an integral heat as a function of a molar ratio of $Gd^{3+}$/1a-e. A solid line corresponds to the best fit curve of data into one set of mathematically determined site models and indicates one molecule ($Gd^{3+}$) being coupled to a respective ligand. A dissociation constant (Kd), an association constant (Ka), the number of $Gd^{3+}$ coupled to a single ligand (N), and a united enthalpy change (ΔH) are obtained by analysis of data. The dissociation and association constants are critical factors for determining a relative stability compared to a ligand (1a-e).
Figure 7B:
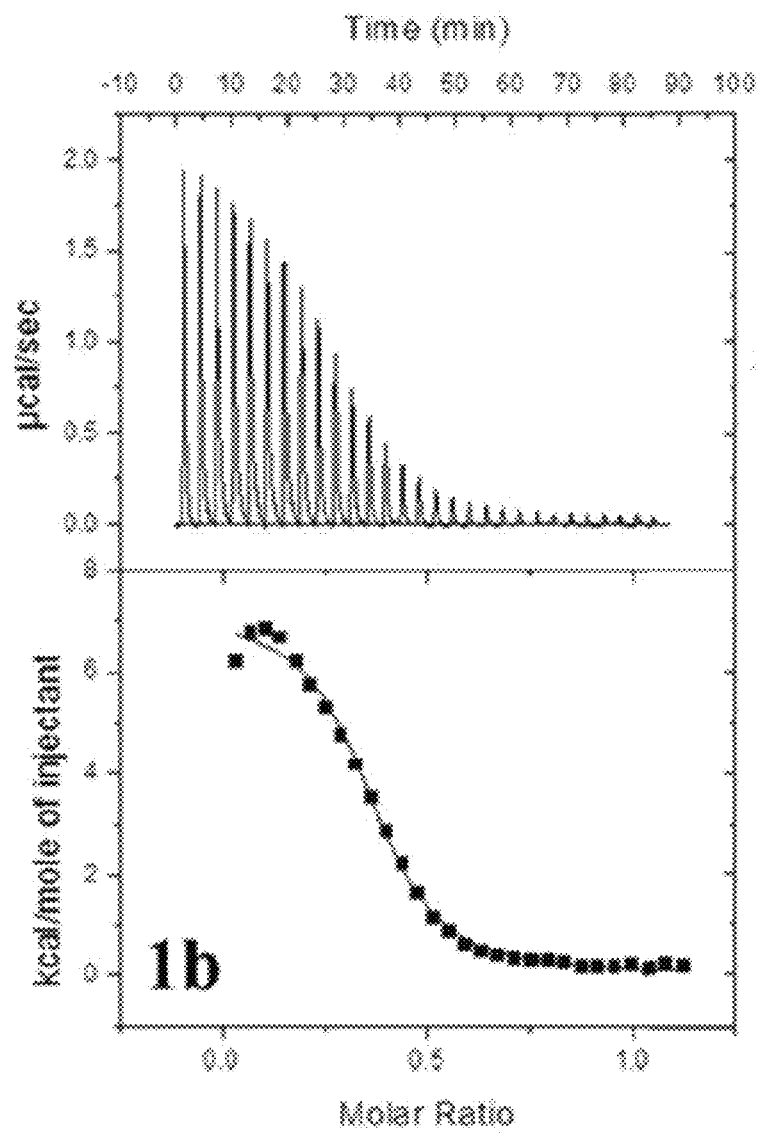
Figure 7C:
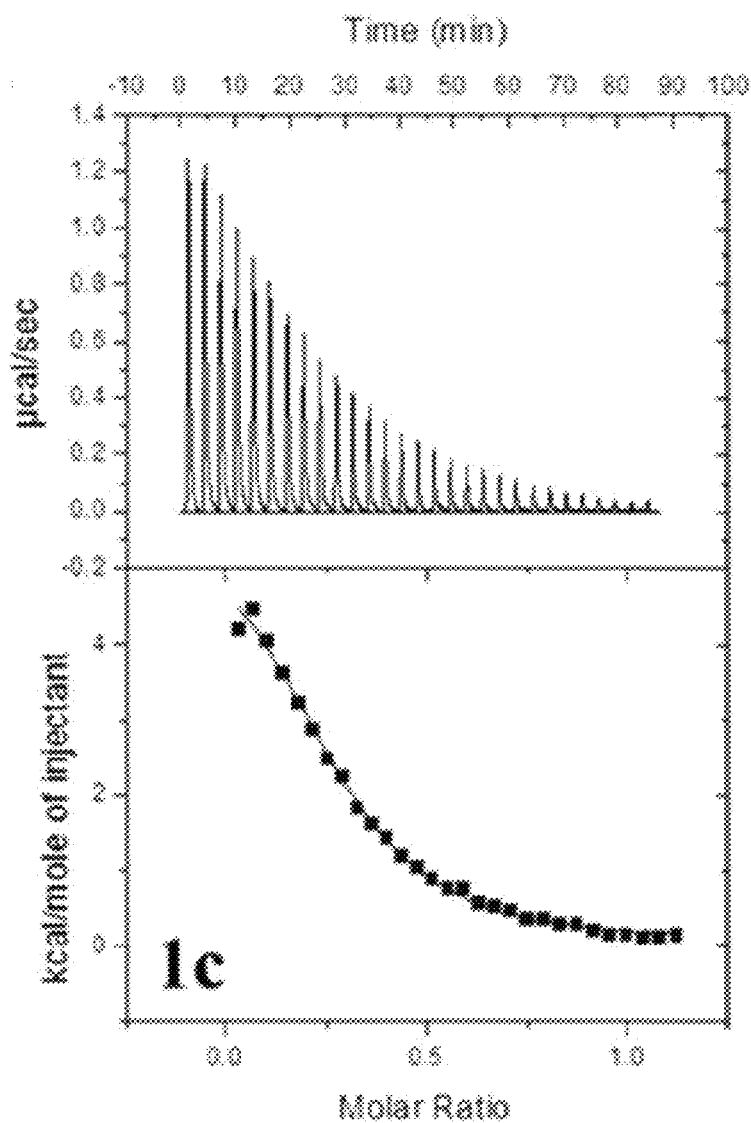
Figure 7D:
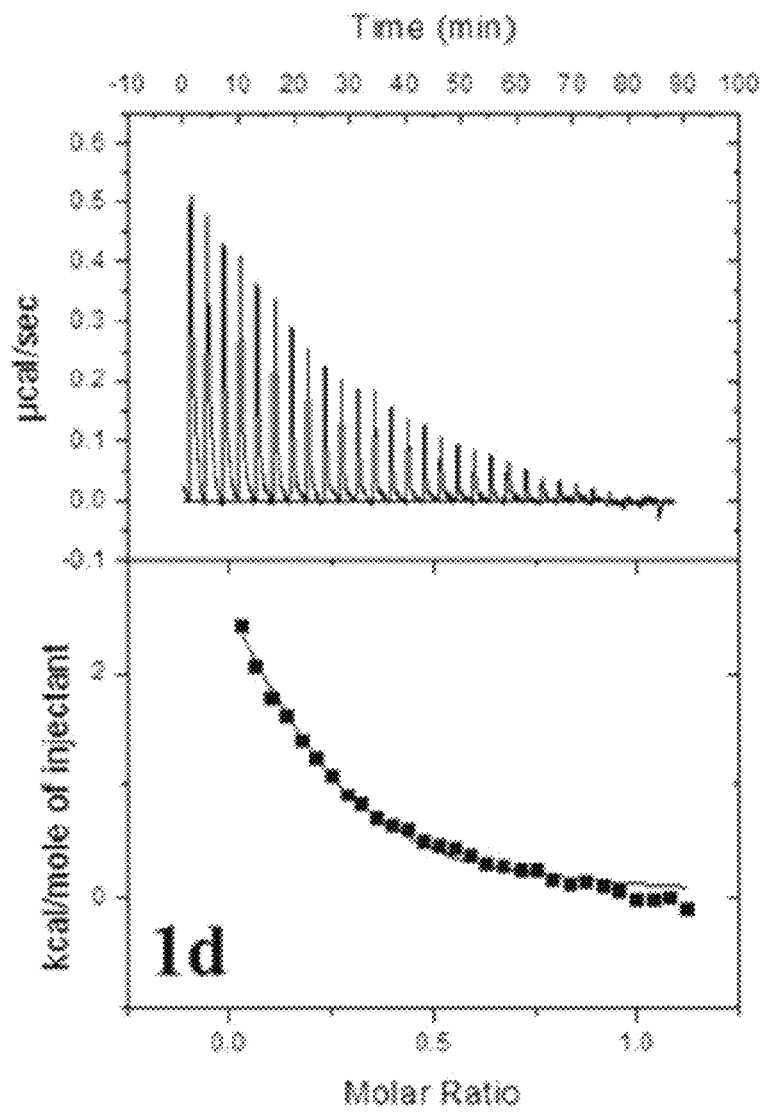
Figure 7E:
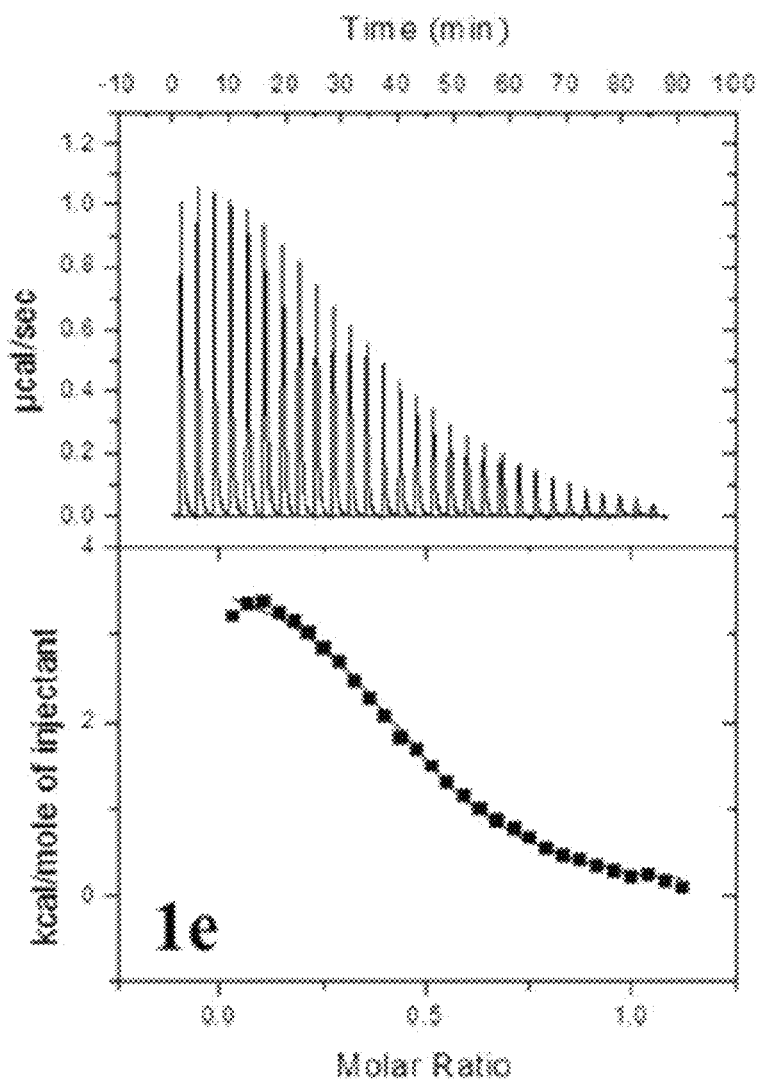

FIG. 6 shows a relative cell toxicity (%) of a normal conjunctival fibroblast obtained using Gd-DOTA and 2b-2. A standard deviation (±SD) is obtained using a triple analysis (n=3).

The cell viability for the 2b to 2e is comparable to that of Dotarem® (FIG. 6). That is, when incubated for 24 h, there is no effect on cell proliferation and cell survival. There is not a substantial difference between the present series 2a to 2e in a cell viability due to the fact that any cytotoxicity does not appear for the present series 2a to 2e over a concentration range needed to acquire the signal intensity enhancement on the MR images.

Embodiment 8: Kinetic Stability in Various pH Ranges

The kinetic stability is expressed as evolution of a water proton relaxation rate ($R_1$) for 2 ([Gd]=1.0 mM) in PBS under various pH conditions (pH: 1, 3, 5, 7, 9 and 11) at a room temperature, as a function of the incubation time. The measurement is executed on a 1.5 T whole body system (GE Healthcare, Milwaukee, Wis., USA).

Figure 9:
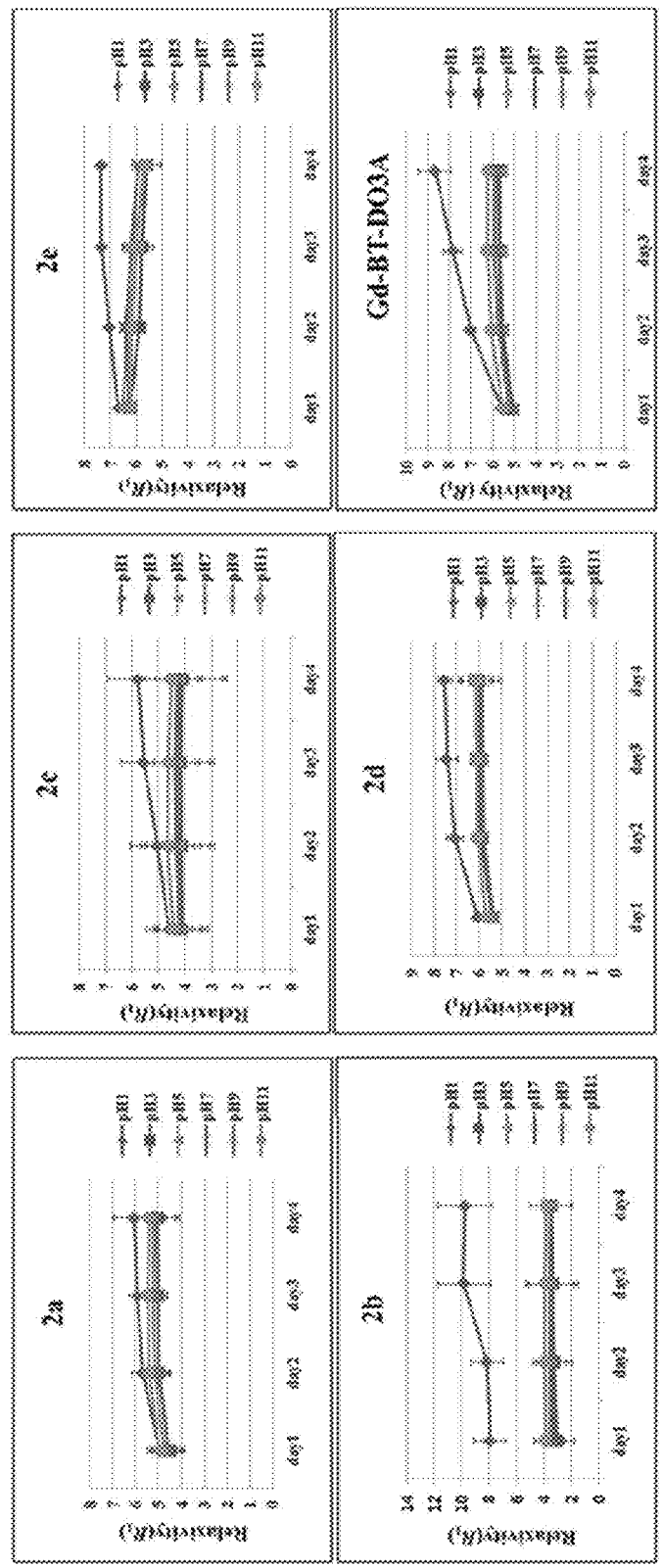
FIG. 9 shows an evolution of $R_1$ for 2 ([Gd]=1.0 mM) in PBS as a function of an incubation time under different pH conditions.

FIG. 9 shows an evolution of $R_1$ for 2 ([Gd]=1.0 mM) in PBS as a function of an incubation time under different pH conditions.

The present series exhibit high kinetic stability over a wide range of pH 3 to 11 (FIG. 9). Especially, the complex 2a exhibits sufficient kinetic stability even at pH 1.

Embodiment 9: Stability Against Hydrolysis in $H_2O$

The contrast agents of the present series 100 mg are dissolved in distilled water 10 mL and is maintained as they are for 72 hours at 50° C. Using HPLC, O.D. (Optical Density) values are read at 197 nm and the stability of the agents is determined. The substances at each retention time are examined using LC Mass Spectroscopy for accurate identification of decomposed products.

A following table 3 is a table showing the hydrolytic stability after 72 hours for the 2a compound. For the complex 2a, the hydrolytic stability falls because hydrolysis into the 2b (Gd-acid) occurs in 72 hours after the complex 2a is kept in water $H_2O$. For the compound 2a, it is confirmed that cis and trans isomers thereof exist.

TABLE 3

|  | 2a (initial) | 2a (50° C./3 day) |
| --- | --- | --- |
| 27.11 min 2a (trans) | 97.73% | 97.43% |
| 30.48 min 2a (cis) | 1.89% | 1.25% |
| 2.31 min 2b | 0.01% | 0.72% |
| 52.24 min | 0.04% | 0.19% |

A following table 4 is a table showing the hydrolytic stability after 72 hours for the 2b compound. For the complex 2b, increase in amount of unknown impurity occurs in 72 hours after the complex 2b is kept in water $H_2O$. For the compound 2b, it is confirmed that cis and trans isomers thereof exist.

TABLE 4

|  | 2b (initial) | 2b (50° C./3 day) |
| --- | --- | --- |
| 2.38 min 2b (trans) | 92.80% | 93.4% |
| 2.88 min 2b (cis) | 3.35% | 2.87% |
| 3.16 min | 0.30% | 0.33% |
| 3.84 min | 0.35% | 0.38% |
| 7.66 min | 0.12% | 0.06% |
| 24.42 min | 0.06% | 0.19% |
| 28.12 min | 0.56% | 0.64% |
| 29.92 min | 0.09% | 0.10% |
| 34.46 min Acid | 0.34% | 0.03% |
| 49.58 min | 0.19% | 0.21% |

A following table 5 is a table showing the hydrolytic stability after 72 hours for the 2c compound. For the complex 2c, very small increase in amount of unknown impurity occurs in 72 hours after the complex 2c is kept in water $H_2O$. Thus, the 2c compound has a relatively good hydrolytic stability. For the compound 2c, it is confirmed that cis and trans isomers thereof exist.

TABLE 5

|  | 2c (initial) | 2c (50° C./3 day) |
| --- | --- | --- |
| 9.10 min 2c (trans) | 91.05% | 93.11% |
| 10.60 min 2c (cis) | 1.35% | 1.19% |
| 2.31 min 2b | 0.06% | 0.11% |
| 2.58% | 0.27% | 0.27% |
| 7.61% | 0.14% | 0.14% |
| 19.86% | 2.22% | 2.30% |
| 40.68 min 1c | 1.65% | 0.002% |
| 45.53 min | 0.16% | 0.18% |
| 49.81 min | 0.09% | 0.11% |

A following table 6 is a table showing the hydrolytic stability after 72 hours for the 2d compound. For the complex 2d, very small increase in amount of unknown impurity occurs in 72 hours after the complex 2d is kept in water $H_2O$. Thus, the 2d compound has a relatively good hydrolytic stability.

TABLE 6

|  | 2d (initial) | 2d (50° C./3 day) |
| --- | --- | --- |
| 6.54 min 2d | 89.67% | 90.10% |
| 8.86 min | 0.30% | 0.30% |
| 7.79 min | 0.30% | 0.36% |
| 33.15 min | 1.20% | 1.12% |
| 40.33 min | 0.16% | 0.007% |
| 40.81 min | 0.14% | 0.14% |
| 43.77 min | 0.27% | 0.25% |
| 44.51 min | 0.23% | 0.22% |
| 46.56 min | 0.19% | 0.18% |

A following table 7 is a table showing the hydrolytic stability after 72 hours for the 2e compound. For the complex 2e, very small increase in amount of unknown impurity occurs in 72 hours after the complex 2e is kept in water $H_2O$. Thus, the 2e compound has a relatively good hydrolytic stability.

TABLE 7

|  | 2e (initial) | 2e (50° C./3 day) |
| --- | --- | --- |
| 17.21 min 2e | 94.88% | 94.66% |
| 2.32 min | 0.04% | 0.04% |
| 4.98 min | 0.09% | 0.07% |
| 23.70 min 2e isomer | 1.36% | 1.57% |
| 40.63 min | 0.03% | 0.05% |
| 42.14 min | 0.01% | 0.05% |
| 43.00 min | 0.05% | 0.05% |
| 44.95 min | 0.05% | 0.05% |
| 45.93 min | 0.04% | 0.03% |
| 46.64 min | 0.02% | 0.01% |
| 48.46 min | 0.03% | 0.03% |
| 49.36 min | 0.18% | 0.18% |

What is claimed is:

1. A DO3A-tranexamic acid compound having a structure of a following chemical formula 1, or an ester compound thereof:

[chemical formula 1]

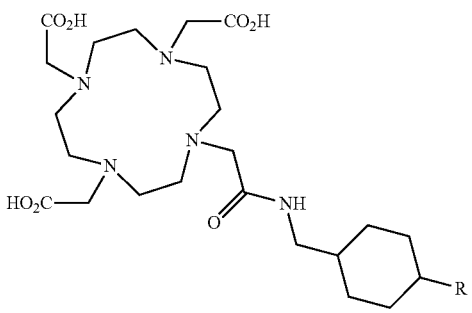

where R is H, $NH_2$ or $CONN(CH_2)_2NH_2$.

2. A method for producing the DO3A-tranexamic acid or the ester compound thereof of claim 1, wherein R=CONH$(CH_2)_2NH_2$ (compound 1c), wherein the method comprises:
   a) adding and agitating bromoacetyl bromide into trans-4 (aminomethyl)cyclohexaneethylcarboxylate hydrochloride to form a first mixture;
   b) adding and agitating DO3A-($^t$BuO)$_3$ to the first mixture to produce DO3A ($^t$BuO)$_3$ tranexamic ethyl ester conjugate;
   c) adding 1,2-diaminoethane to the DO3A ($^t$BuO)$_3$ tranexamic ethyl ester conjugate to form a second mixture;
   d) removing a solvent from the second mixture under a low pressure and then dissolving the resultant product in methanol and then performing silica gel chromatography thereto;
   e) adding TFA to the product subjected to the chromatography to deprotect a tert-butyl group; and
   f) drying the thus-resulting product in a vacuum state to obtain the DO3A-tranexamic acid or the ester compound thereof.

3. A method for producing the DO3A-tranexamic acid or the ester compound thereof of claim 1, wherein R=$NH_2$ (compound 1d), wherein the method comprises:
   a) adding and agitating di-tert-butyl dicarbonate to trans-1,4-diaminocyclohexane to form a first mixture;
   b) adding and agitating bromoacetyl bromide to the first mixture to form a second mixture;
   c) adding and agitating DO3A-($^t$BuO)$_3$ to the second mixture to produce DO3A ($^t$BuO)$_3$ tranexamic amine conjugate;
   d) removing a solvent from the resultant product under a low pressure and then dissolving the resultant product in methanol and then performing silica gel chromatography thereto;
   e) adding TFA to the product subjected to the chromatography to deprotect a tert-butyl group; and
   f) drying the thus-resulting product in a vacuum state to obtain a DO3A-tranexamicamine compound.

4. A method for producing the DO3A-tranexamic acid or the ester compound thereof of claim 1, wherein R=H (compound 1e), wherein the method comprises:
   a) adding and agitating bromoacetyl bromide to (aminomethyl)cyclohexane to prepare a first mixture;
   b) adding and agitating DO3A-($^t$BuO)$_3$ to the first mixture to prepare DO3A-($^t$BuO)$_3$ tranexamic conjugate;
   c) removing a solvent from the resultant product under a low pressure and then dissolving the resultant product in methanol and then performing silica gel chromatography thereto;
   d) adding TFA to the product subjected to the chromatography to deprotect a tert-butyl group; and
   e) drying the thus-resulting product in a vacuum state to obtain the DO3A-tranexamic acid or the ester compound thereof.

5. A composition for a complex ligand (L), wherein the composition contains the DO3A-tranexamic acid or the ester compound thereof of claim 1.

6. A complex containing the DO3A-tranexamic acid or the ester compound thereof of claim 1 as a ligand (L), wherein the complex contains a metal atom coordinated with the ligand.

7. The complex of claim 6, where the metal atom is gadolinium (Gd).

8. A MRI contrast agent containing the complex of claim 6 as an effective component.

9. The MRI contrast agent of claim 8, wherein the contrast agent has ECF (extracelluar fluid) image contrast function.

* * * * *